US010130472B2

United States Patent
O'Beirne et al.

(10) Patent No.: US 10,130,472 B2
(45) Date of Patent: *Nov. 20, 2018

(54) DEVICES AND METHODS FOR TREATING VALVULAR REGURGITATION

(71) Applicant: Medtronic Vascular, Inc., Santa Rosa, CA (US)

(72) Inventors: Patricia O'Beirne, Ballybrit (IE); Nasser Rafiee, Andover, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 23 days.

This patent is subject to a terminal disclaimer.

(21) Appl. No.: 15/247,631

(22) Filed: Aug. 25, 2016

(65) Prior Publication Data

US 2017/0049570 A1   Feb. 23, 2017

Related U.S. Application Data

(60) Continuation of application No. 14/317,994, filed on Jun. 27, 2014, now Pat. No. 9,452,048, which is a division of application No. 12/326,525, filed on Dec. 2, 2008, now Pat. No. 8,795,352.

(60) Provisional application No. 61/045,021, filed on Apr. 15, 2008.

(51) Int. Cl.
*A61F 2/24* (2006.01)
*A61B 17/04* (2006.01)
*A61B 17/00* (2006.01)

(52) U.S. Cl.
CPC .......... *A61F 2/2445* (2013.01); *A61F 2/2427* (2013.01); *A61F 2/2442* (2013.01); *A61F 2/2466* (2013.01); *A61B 17/0487* (2013.01); *A61B 2017/00243* (2013.01); *A61B 2017/00783* (2013.01); *A61B 2017/0409* (2013.01); *A61B 2017/0441* (2013.01); *A61B 2017/0496* (2013.01)

(58) Field of Classification Search
CPC ........ A61F 2/24; A61F 2/2442; A61F 2/2445; A61F 2/246; A61F 2/2409; A61B 17/0401; A61B 17/0487; A61B 2017/0409; A61B 2017/0496; A61B 2017/0464; A61B 2017/00243; A61B 2017/00783
USPC ......................................... 623/2.11; 606/232
See application file for complete search history.

(56) References Cited

U.S. PATENT DOCUMENTS

| | | | |
|---|---|---|---|
| 6,599,311 B1 | 7/2003 | Biggs et al. | |
| 8,333,777 B2 | 12/2012 | Schaller et al. | |
| 9,452,048 B2 * | 9/2016 | O'Beirne | A61F 2/2466 |
| 2004/0162610 A1 * | 8/2004 | Liska | A61F 2/2454 |
| | | | 623/2.11 |
| 2004/0186566 A1 * | 9/2004 | Hindrichs | A61B 17/00234 |
| | | | 623/2.37 |

(Continued)

*Primary Examiner* — Melanie Tyson
(74) *Attorney, Agent, or Firm* — Medler Ferro Woodhouse & Mills PLLC

(57) ABSTRACT

A system for treating mitral valve regurgitation includes a tensioning device having a plurality of helical anchors and a tensioning filament. One embodiment of the invention includes a method for attaching a tensioning device to the annulus of a mitral valve in a trans-leaflet configuration, and applying a tension force to the tension filament in order to exert force vectors on the annulus, thereby reshaping the mitral valve annulus so that the coaption of the anterior and posterior leaflets of the mitral is improved during ventricular contraction.

16 Claims, 10 Drawing Sheets

(56) References Cited

U.S. PATENT DOCUMENTS

| | | |
|---|---|---|
| 2004/0193217 A1 | 9/2004 | Lubbers |
| 2004/0260394 A1* | 12/2004 | Douk .................... A61F 2/2433 623/2.36 |
| 2005/0177180 A1 | 8/2005 | Kaganov et al. |
| 2006/0122633 A1 | 6/2006 | To et al. |
| 2006/0287661 A1 | 12/2006 | Bolduc et al. |
| 2007/0083259 A1* | 4/2007 | Bloom .................. A61F 2/2454 623/2.11 |
| 2007/0118151 A1 | 5/2007 | Davidson |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2008/0027560 A1 | 1/2008 | Jackson et al. |

* cited by examiner

DEVICES AND METHODS FOR TREATING VALVULAR REGURGITATION

RELATED APPLICATIONS

This application is a Continuation of and claims priority to U.S. patent application Ser. No. 14/317,994 filed Jun. 27, 2014, now U.S. Pat. No. 9,452,048, which is a Division of U.S. patent application Ser. No. 12/326,525, filed Dec. 2, 2008, now U.S. Pat. No. 8,795,352, which claims the benefit of, and priority to, U.S. Provisional Patent Application 61/045,021 filed on Apr. 15, 2008. The entirety of that application is incorporated herein by reference.

FIELD OF THE INVENTION

This invention relates generally to the treatment of mitral valve regurgitation and particularly to a method and device to improve mitral valve coaption in a diseased heart.

BACKGROUND

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the mitral valve into the left ventricle. The left ventricle contracts and pumps blood through the aortic valve into the aorta and to the vascular system.

The mitral valve consists of two leaflets (anterior and posterior) attached to a fibrous ring or annulus. In a healthy heart, the mitral valve leaflets close during contraction of the left ventricle and prevent blood from flowing back into the left atrium. Due to various cardiac diseases, however, the mitral valve annulus may become distended causing the leaflets to remain partially open during ventricular contraction and thus allow regurgitation of blood into the left atrium. This results in reduced ejection volume from the left ventricle, causing the left ventricle to compensate with a larger stroke volume. However, the increased workload eventually results in dilation and hypertrophy of the left ventricle, further enlarging and distorting the shape of the mitral valve. If left untreated, the condition may result in cardiac insufficiency, ventricular failure, and ultimately death.

It is common medical practice to treat mitral valve regurgitation by either valve replacement or repair. Valve replacement involves an open-heart surgical procedure in which the patient's mitral valve is removed and replaced with an artificial valve. This is a complex, invasive surgical procedure with the potential for many complications and a long recovery period.

Mitral valve repair includes a variety of procedures to repair or reshape the leaflets to improve closure of the valve during ventricular contraction. If the mitral valve annulus has become distended, a frequent repair procedure involves implanting an annuloplasty ring on the mitral valve annulus. The annuloplasty ring generally has a smaller diameter than the annulus, and when sutured to the annulus the annuloplasty ring draws the annulus into a smaller configuration, bringing the mitral valve leaflets closer together, and allowing improved closure during ventricular contraction. Annuloplasty rings may be rigid, flexible or a combination, having both rigid and flexible segments. Rigid annuloplasty rings have the disadvantage of causing the mitral valve annulus to be rigid and unable to flex in response to the contractions of the ventricle, thus inhibiting the normal, three dimensional movement of the mitral valve that is required for it to function optimally. Flexible annuloplasty rings are frequently made of Dacron® fabric and must be sewn to the annular ring with a line of sutures. This eventually leads to scar tissue formation and loss of flexibility and function of the mitral valve. Similarly, combination rings must generally be sutured in place and also cause scar tissue formation and loss of mitral valve flexibility and function.

Another approach to treating mitral valve regurgitation requires a flexible elongated device that is inserted into the coronary sinus and adapts to the shape of the coronary sinus. The device then undergoes a change that causes it to assume a reduced radius of curvature and, as a result, causes the radius of curvature of the coronary sinus and the circumference of the mitral annulus to be reduced. While likely to be effective for modest changes in the size or shape of the mitral annulus, this device may cause significant tissue compression in patients requiring a larger change in the configuration of the mitral annulus. Alternatively, the coronary sinus in a particular individual may not wrap around the heart far enough or may not be in an optimum position to allow effective encircling of the mitral valve, making this treatment ineffective. Furthermore, leaving a device in the coronary sinus may result in formation and breaking off of thrombus that may pass into the right atrium, right ventricle, and ultimately the lungs causing a pulmonary embolism. Another disadvantage is that the coronary sinus is typically used for placement of a pacing lead, which may be precluded with the placement of the prosthesis in the coronary sinus.

It would be desirable, therefore to provide a method and device for reducing mitral valve regurgitation that would use minimally invasive surgical techniques, but would overcome the limitations and disadvantages inherent in the devices described above.

BRIEF SUMMARY OF THE INVENTION

One aspect of the invention provides a system for treating mitral valve regurgitation comprising a delivery catheter and a tensioning device. The tensioning device comprises a plurality of helical anchors and a tension filament. The anchors are deployed from a delivery catheter such that they are implanted in the annulus of the mitral valve, and the tension filament is adjusted so that the shape of the annulus is changed in order to achieve coaption of the mitral valve leaflets.

Another aspect of the invention provides a method for treating mitral valve regurgitation and includes preloading a tensioning device into an internal lumen of an elongated delivery catheter or delivery member. The tensioning device comprises a plurality of helical anchors, a tension filament, and at least one locking device to secure the tensioning device after the shape of a mitral valve has been changed. The method further comprises deploying the tensioning device from the catheter adjacent to the mitral valve and embedding the anchors into the annulus such that the tension filament extends through the anchors. Next, a tension force is applied to the tension filament, causing the posterior and anterior sides of the mitral valve annulus to be drawn closer to each other.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION

The invention will now be described by reference to the figures wherein like numbers refer to like structures. The terms "distal" and "proximal" are used herein with reference to the treating clinician during the use of the catheter system; "Distal" indicates an apparatus portion distant from, or a direction away from the clinician and "proximal" indicates an apparatus portion near to, or a direction towards the clinician.

The current invention discloses devices and methods for treating regurgitation in cardiac valves. While these devices and methods are described below in terms of being used to treat mitral valve regurgitation, it will be apparent to those skilled in the art that the devices could be used on other cardiac valves, also. Tensioning devices of the current invention comprise helical anchors, at least one tension filament, and locks. The tensioning devices are used to modify the shape of heart valves for treating valvular regurgitation. The systems of the current invention comprise the tensioning devices and the delivery members for placing the tensioning devices adjacent a heart valve annulus. The devices and systems of the current invention can be delivered to a patient's valve annulus via catheter through the patient's vasculature, via a tubular access port (or other port) as part of a minimally invasive surgical approach, or via an open heart surgical delivery.

Figure 1:
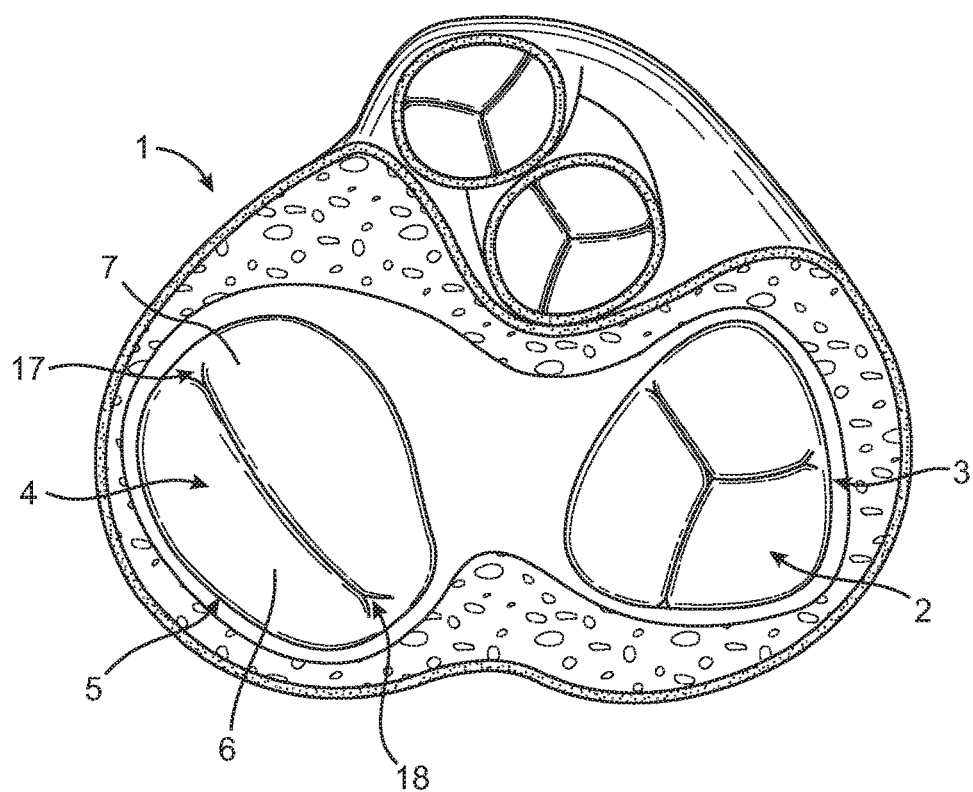
FIG. 1 is a plan view of a heart showing the location of the heart valves.

Referring to the drawings, FIG. 1 shows a plan view of a cross-section of a heart 1 having tricuspid valve 2 and tricuspid valve annulus 3. Mitral valve 4 is adjacent mitral valve annulus 5. Mitral valve 4 is a bicuspid valve having anterior cusp 7 and posterior cusp 6. Anterior cusp 7 and posterior cusp 6 are often referred to, respectively, as the anterior and posterior leaflets. Also shown in the figure are the posterior commisure 17 and the anterior commisure 18.

Figure 2:
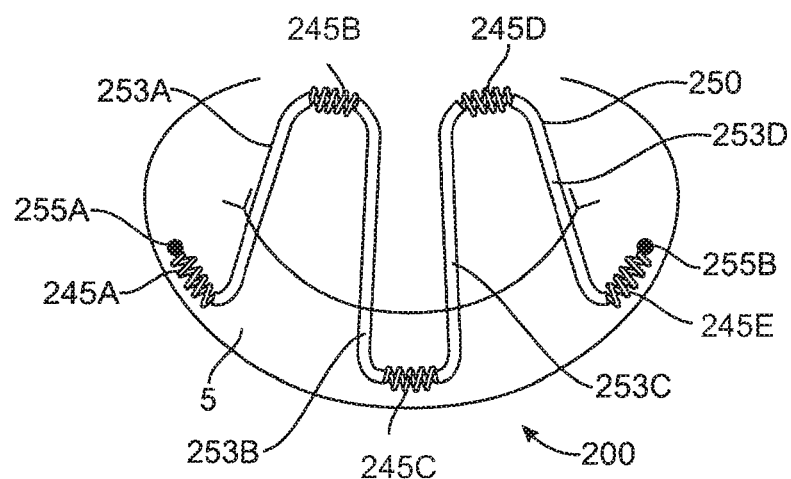
FIG. 2 shows one embodiment of a tensioning device attached to a mitral valve annulus according to the current invention.

FIG. 2 shows one embodiment of a tensioning device 200, made in accordance with the present invention, attached to a mitral valve annulus 5. Tensioning device 200 comprises three helical anchors 245A, 245B, and 245C, implanted along the posterior portion of the annulus between the posterior commisure and the anterior commisure. Tensioning device 200 further comprises a pair of helical anchors 245D and 245E implanted along the anterior portion of the valve annulus between the left and right trigones. A tension filament 250 is disposed in the inner channels of the helical anchors. Tensioning device 200 comprises a trans-leaflet tensioning device whereby tension filament 250 is configured to cross from one leaflet to another in a generally zig-zag pattern. In one embodiment shown in FIG. 2, tension filament 250 comprises a plurality of trans-leaflet portions 253A to 253D. Each of the trans-leaflet portions 253A to 253D extend from a helical anchor implanted in the anterior leaflet 7 to another helical anchor implanted in the posterior leaflet 6. In this embodiment, trans-leaflet portion 253A extends from helical anchor 245A to helical anchor 245E; trans-leaflet portion 253B extends from helical anchor 245E to helical anchor 245B; trans-leaflet portion 253C extends from helical anchor 245B to helical anchor 245D and trans-leaflet portion 253D extends from helical anchor 245D to helical anchor 245C. In this embodiment, a first filament lock 255A is located at the end of the tension filament that passes through the helical anchor 245A that is adjacent to the anterior commisure and a second filament lock 255B is located at the end of the tension filament that passes through the helical anchor 245C that is adjacent to the posterior commisure. The force vectors resulting from tension on filament 250 are exerted through anchors 245A to 245E and cause the shape of mitral valve 5 to change, which in turn, draws the valve leaflets closer together and improves coaption. The direction and magnitude of the force vectors exerted at each anchor are determined by placement of the anchors along the annulus and the amount of tension placed on the filament.

Those with ordinary skill in the art will appreciate that the number of helical anchors implanted into the valve annulus may vary depending on a particular application. In at least one embodiment of the invention, fewer than five helical anchors are implanted in the valve annulus to draw the two sides of the annulus closer together. In another embodiment of the invention, more than five anchors are implanted in the valve annulus to draw the sides of the annulus closer together. In one embodiment, the number of implanted helical anchors is as few as three and as many as seven or more. The number of helical anchors implanted into the valve annulus may be determined by such factors as, but not limited to, the size of the valve annulus, the size of the helical anchors, the degree of valve regurgitation to be corrected and the amount of tension required to provide coaption.

Figure 3:
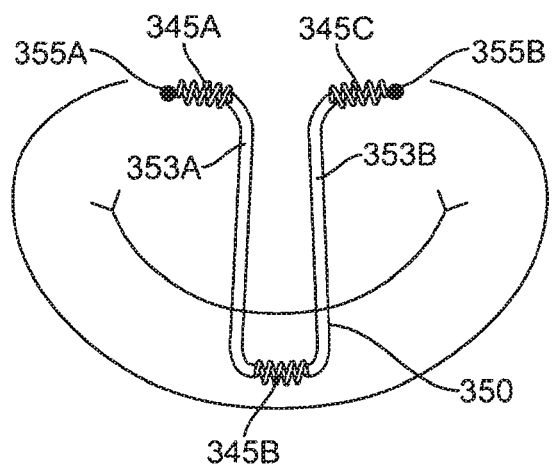
FIG. 3 shows another embodiment of a tensioning device attached to a mitral valve annulus according to the current invention.

FIG. 3 illustrates another embodiment of a tensioning device 300 in accordance with the present invention. In this embodiment, system 300 includes three helical anchors 345A to 345C and tensioning filament 350. Tensioning filament 350 includes two trans-leaflet portions, portion 353A extending from helical anchor 345A to helical anchor 345B and portion 353B extending from helical anchor 345B to helical anchor 345C. System 300 further includes a first filament lock 355A located at the end of the tension filament that passes through helical anchor 345A and a second filament lock 355B located at the end of the tension filament that passes through helical anchor 345C.

As described above, the tensioning devices of the current invention are attached to the annulus of a mitral valve using helical anchors. In one embodiment, the tensioning devices are delivered to, and implanted in, a beating heart using a minimally invasive surgical technique. In another embodiment, the tensioning devices are delivered and implanted via a catheter based delivery system that accesses the valve through the vascular system. Where devices are delivered using minimally invasive surgical procedures, the delivery instruments can be inserted through the wall of the atrium at a location directly adjacent to the posterior commisure. If the devices are delivered to the atrium via catheter, the catheter can enter the atrium through an opening created in the septal wall between the left and right atrium. The devices of the invention can also be implanted in the valves of a temporarily stopped heart and in one embodiment the device is delivered via open heart surgery. Devices, systems, and methods for changing the shape of the annulus of a cardiac valve using devices having helical anchors are described in United States Patent Applications having the following publication numbers, all of which are incorporated herein by reference thereto: US 2007/0244557; US 2007/0244553; US 2007/0244554; US 2007/0244555; and US 2007/0244556.

Figure 4A:
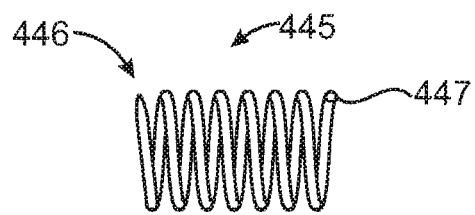
FIGS. 4A and 4B show a helical anchor for a tensioning device according to the current invention.
Figure 4B:
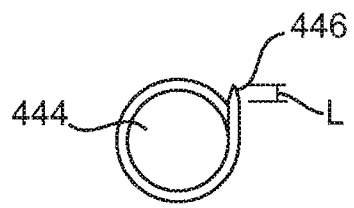

Referring again to the drawings, FIGS. 4A through 8B illustrate the components of an embodiment of an annulus modification system for modifying a heart valve according to the current invention. Referring first to FIGS. 4A and 4B, there is shown a helical anchor 445 for a tensioning device according to the current invention. Helical anchor 445 comprises an elongate coiled member having a tissue penetrating tip 446 at a distal end and a proximal end 447 that is operably connected to a helical anchor driver.

The coils of the helical anchor 445 define a structure having a generally circular shape and a tip 446 that extends on a tangent away from the circular perimeter of the helical anchor. Angling the sharpened tip 446 away from the exterior perimeter of the helical anchor makes it easier for the tip to penetrate a valve annulus when the helical anchor is being rotated out of a delivery member and along an anchor guide. In some embodiments, the length L of the sharpened tip portion is in the range of 0.045 inches to 0.065 inches. One embodiment of a helical anchor has a tip length greater than 0.065 inches, another embodiment has a tip length less than 0.045 inches, and one embodiment of a helical anchor according to the current invention has a tip length of 0.055 inches.

Helical anchor 445 comprises a biocompatible metallic or polymeric material having suitable resiliency. In one embodiment, helical anchor 445 comprises stainless steel, in another embodiment, the helical anchor comprises 35NLT, and in yet another embodiment the helical anchor comprises MP35N. The diameter of the metallic or polymeric member that is coiled to make the helical anchor can vary based on such factors as, but not limited to, the desired flexibility, the size of the annulus, and the delivery method. Some embodiments include helical anchors made from wires with diameters in a range of 0.017 inches-0.025 inches. One embodiment is made from a material with a diameter smaller than 0.017 inches, another embodiment is made from a material with a diameter larger than 0.025 inches, and yet another embodiment is made from a material having a diameter of 0.02 inches.

The coils of the helical anchor define an inner channel 444 for passage of a tension filament. The helical anchor has an outer diameter defining the exterior of the helical anchor and an inner diameter defining the channel or lumen through the helical anchor. Some embodiments of the invention include helical anchors having inner channel diameters in the range of 0.10 inches-0.20 inches. One embodiment includes a helical anchor with an inner channel diameter smaller than 0.10 inches, another embodiment has a helical anchor with an inner channel diameter larger than 0.200 inches, and yet another embodiment has a helical anchor with an inner channel diameter of 0.11 inches. Outer diameters for the helical anchors are in the range of 0.150 inches-0.250 inches. One embodiment includes a helical anchor with an outer diameter smaller than 0.150 inches, another embodiment has a helical anchor with an outer diameter larger than 0.250 inches, and yet another embodiment has a helical anchor with an outer diameter of 0.150 inches.

The distance between each coil defines the coil pitch, and the pitch can also be expressed as the number of coils per inch. The number of coils per inch for the helical anchors of the current invention can vary based on the desired degree of flexibility and resiliency. Some embodiments include helical anchors having coils per inch in the range of 10 to 20. One embodiment of a helical anchor has less than 10 coils per inch, one embodiment of a helical anchor has more than 20 coils per inch, and one embodiment of a helical anchor according to the current invention has 12 coils per inch. An additional embodiment of the current invention includes helical anchors having 14 coils per inch.

In addition to the pitch, the length of the helical anchors of the various embodiments of the invention can vary based on the size of a patient's valve annulus and the number and location of helical anchors needed to modify the shape of the annulus. In one embodiment of the invention, multiple helical anchors are implanted.

Some embodiments of the invention include helical anchors having a length in the range of 0.20 inches to 0.5 inches. At least one embodiment has at least one helical anchor longer than 0.5 inches and another embodiment has at least one helical anchor shorter than 0.20 inches. One embodiment of the invention uses a plurality of helical anchors having the same length to modify the shape of a heart valve annulus. Another embodiment of the invention uses a plurality of helical anchors where not all of the helical anchors have the same length.

The flexibility of the helical anchor can be controlled by the diameter of the wire or other material used to make the helical anchor and the number of coils per inch. As will be described further below, a tension filament will be placed through the inner channel of one or more helical anchors that are implanted along a heart valve annulus. The tension filament will then be manipulated to exert a force on the helical anchors to draw the two sides of the annulus closer together, thereby modifying the shape of the valve annulus and improving coaption of the valve leaflets.

Helical anchors 445 comprise a plurality of individual coils. The plurality of coils forms a generally cylindrical inner channel 444 that can accommodate an anchor guide and through which a portion of a tension filament will be disposed. In operation, the inner channel diameter, the coil pitch and the length of the tip 446 of the helical anchor may be determined to provide a specific depth of penetration of the helical anchor 445 as it is threaded along the valve annulus.

Figure 5:
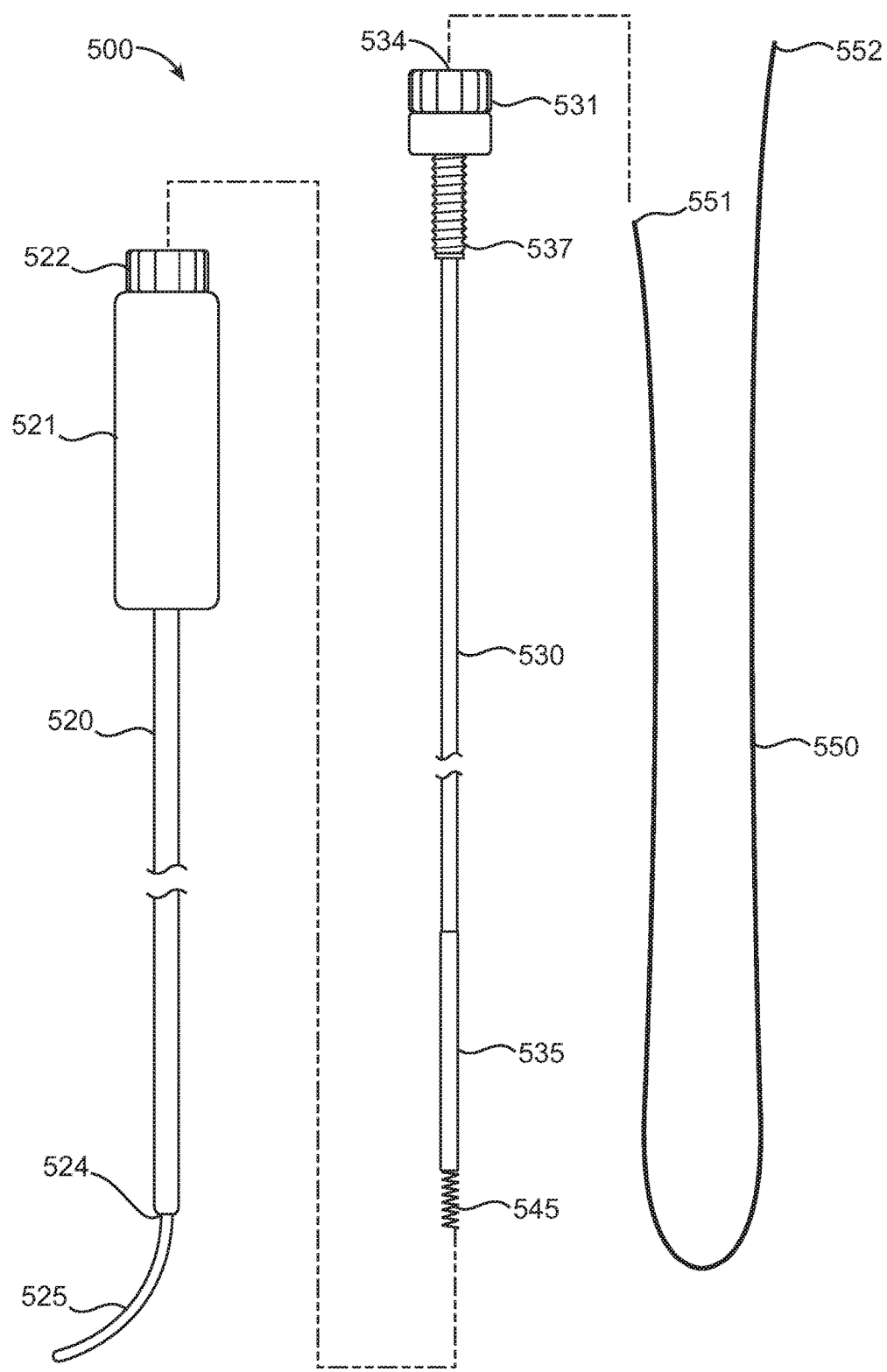
FIG. 5 shows a system for modifying the shape of a heart valve annulus according to the current invention.

FIG. 5 shows an embodiment of a system 500 for changing the shape of a valve annulus according to the current invention. This embodiment comprises an elongated generally tubular delivery member 520 having a handle 521 and a handle cap 522 on the proximal end of the delivery member 520. The distal end of the delivery member 520 includes an anchor guide 525 and a distal opening 524 of the driver lumen that communicates through the length of the delivery member. Anchor guide 525 is configured to conform to the shape of at least a portion of the valve annulus when the anchor guide is placed next to a valve annulus at the treatment site.

An elongated helical anchor driver 530 includes a driver knob 531 on the proximal end of the driver and a threaded portion 537 adjacent the knob. A distal portion 535 of the driver is connected to a helical anchor 545. The system also includes a flexible elongated tension filament 550 having a first end 551 and a second end 552. The tension filament 550 is delivered to the treatment site in a looped configuration with first and second ends extending outside the patient's body during the implantation procedure.

To use the system, the first end 551 of the tension filament 550 is threaded into a tension filament lumen 534 at the proximal end of the driver and out through an inner channel of the helical anchor 545. The tension filament is then threaded into the driver lumen and into a tension filament lumen (not shown) in the anchor guide 525. The tension filament exits the end of the anchor guide and is routed back up through the driver lumen and exits the handle 521 through another tension filament lumen (not shown). For the delivery of each successive anchor of the system, the ends of the tension filament can be threaded through additional drivers, helical anchors and/or delivery members based on the method of delivery and where the new helical anchor will be implanted relative to the preceding helical anchor.

Figure 6A:
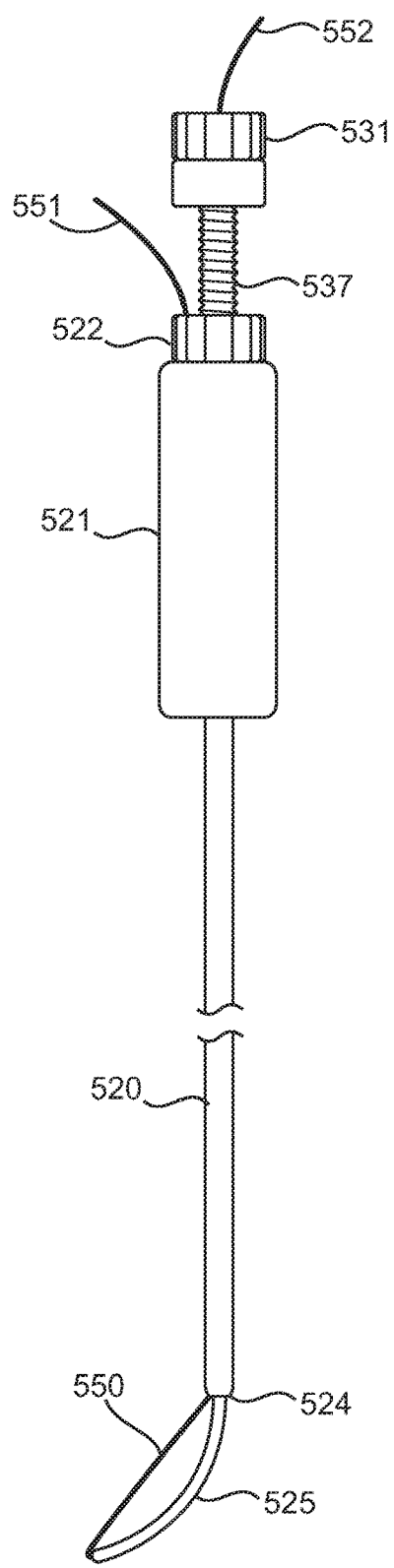
FIGS. 6A and 6B show an embodiment of an annulus modification system according to the current invention

Referring to FIG. 6A, the driver 530 is inserted into the driver lumen of the delivery member 520 and advanced until the threaded portion 537 makes contact with a complementary threaded portion (not shown) on the interior of the delivery member handle 521. When the driver has been advanced to the point where the threaded portion on the driver makes contact with the threaded portion on the handle, the helical anchor 545 will be located adjacent to the anchor guide 525. The anchor guide 525 would then be aligned with a valve annulus and placed on the annulus in the desire location for implanting the helical anchor such that the anchor guide is laying directly on the valve annulus and directly adjacent the wall of the heart chamber. The anchor guide will be shaped so that it conforms to the shape of the annulus at the point of desired anchor implantation. In at least one embodiment, the same anchor guide can be used for implanting all helical anchors. In at least one embodiment of the invention, multiple anchor guides are used for implanting the helical anchors. In at least one embodiment, each of the multiple anchor guides used for implanting a plurality of helical anchors is shaped to correspond to the geometry of a specific portion of the valve annulus to be treated.

Once anchor guide 525 is in the correct position, the driver is rotated via handle 531 and the anchor is rotated into the valve annulus. In at least one embodiment, the rotation occurs such that the tip of the anchor is rotated toward the wall of the heart as the guide rests on the top of the annulus and the system is viewed from above. In at least one other embodiment, the rotation occurs such that the tip of the anchor is rotated away from the wall of the heart as the guide rests on the top of the annulus and the system is viewed from above.

In at least one embodiment, the delivery member is left inside of a patient's body and the driver is withdrawn from the delivery member for each successive helical anchor. The tension filament is threaded into an additional helical anchor and driver. The new driver is then inserted into the delivery member and advanced so that the helical anchor is at the distal opening in the delivery member. The anchor guide is then manipulated so that it is placed on the portion of the valve annulus where the additional helical anchor is desired, and the helical anchor is implanted as described above. The other helical anchors can be implanted using the same delivery member, or the delivery member can be withdrawn and the other helical anchors implanted using additional delivery members and drivers as described above.

Figure 6B:
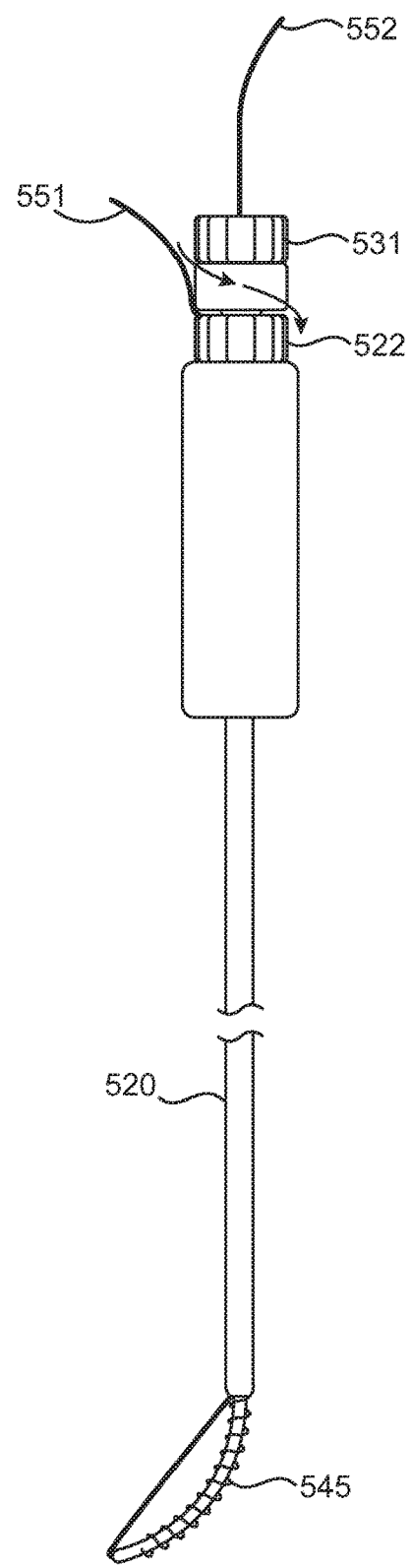

Referring now to FIG. 6B, the driver knob 531 is rotated so that the threaded portion 537 on the driver is screwed into the complementary threaded portion of the delivery member 520. As the driver is threaded into the delivery member, the distal portion of the driver rotates and moves toward the distal opening 524 of the delivery member until the distal end of the helical anchor is extended from the delivery member and the distal end is rotated into and out of the valve annulus while the helical anchor moves along the anchor guide.

In some embodiments of the systems of the current invention, the helical anchor is engaged to the distal tip of the driver and the driver and helical anchor are placed in the delivery member such that the anchor guide is already in the inner channel of the helical anchor. In other embodiments, the extended distal tip of the helical anchor catches the anchor guide, as the distal end of the helical anchor extends from the distal opening of the delivery member, and the helical anchor is rotated onto and along the delivery guide and into the annulus as the driver is threaded into the delivery member.

Once the helical anchor is implanted, the anchor guide is withdrawn into the delivery member. After the anchor guide is removed from the inner channel of the helical anchor, a portion of the tension filament remains disposed in the helical anchor such that one end of the tension filament extends from the distal end of the helical anchor and the other end of the tension filament extends from the proximal end of the helical anchor.

The tension filament slides freely through the tension filament lumens or other portions of the delivery member and driver while they are being withdrawn, and it can be completely removed from those portions of the system such that the ends extend outside of a patient's body while a portion of the tension filament is disposed in the inner channel of the helical anchor implanted in the patient's heart valve annulus.

The components of the system can be made from any suitable biocompatible material. Based on the delivery method, the delivery members can be made of flexible, biocompatible polymeric material such as, but not limited to, polyurethane, polyethylene, nylon and polytetrafluoroethylene (PTFE); or they can be made can be made from rigid plastics or metals such as stainless steel or other suitable metal. The delivery members can also be made from a combination of two or more of these materials.

The drivers can also be made from flexible, biocompatible polymeric material such as, but not limited to, polyurethane, nylon, polytetrafluoroethylene (PTFE) and polyethylene. Portions of the driver can be made from rigid plastics or metals such as stainless steel or other suitable metals as long as the distal portion of the driver is made from a flexible material that will allow it to negotiate curved portions of the delivery member. In one embodiment, the proximal portion of the driver is a braided member formed from a plurality of metallic filaments. In other embodiments, the drivers can include portions made from polymeric filaments or a combination of metallic and polymeric filaments. The materials used to manufacture the driver may be chosen to provide a determined flexibility or stiffness along the length of the driver.

The lumens of the delivery members and drivers of the current invention can be coated with a lubricious material such as silicone, polytetrafluroethylene (PTFE), or a hydrophilic coating. The lubricious interior surface of a delivery member facilitates the longitudinal movement of a driver.

The anchor guides can be made from a suitable biocompatible metallic or polymeric material or combinations thereof. The anchor guides of the current invention can be made from a flexible material, but the material must be hard enough to resist penetration by the sharpened distal end of a helical anchor. In one embodiment of the invention, the anchor guide is made from stainless steel. In another embodiment, the anchor guide is made from a shape memory material that assumes a predetermined shape upon exiting delivery member 520. In one embodiment of the invention, the tubular delivery member and the anchor guide are formed as a unitary piece from a biocompatible material. In other embodiments, the delivery members and anchor guides are fashioned as separate pieces that are joined together by, for example, adhesive, welding or any other manner known in the art.

The tension filaments of the current invention are elongated, flexible filaments of any suitable biocompatible material. In one embodiment, the tension filament comprises a monofilament. In other embodiments the tension filaments may comprise a braid of a plurality of filaments of the same material or of filaments from different materials. Still other embodiments of tension filaments comprise a braided sheath with a single filament core, or a braided sheath with a braided core. The tension filaments may be composed of biocompatible material such as, but not limited to, nylon or polyester.

The tension filaments may be constructed from material that will not stretch or it may be pre-stressed to prevent the tension filament from elongating after the annuloplasty devices of the current invention are implanted in a heart valve annulus. In one embodiment, the tension filament is made from a pre-stretched ultra-high-molecular-weight polyethylene. Various embodiments of the invention include tension filaments having diameters in the range of 0.015 inches and 0.050 inches in diameter. In one embodiment of the invention the tension filament has a diameter smaller than 0.015 inches and in another embodiment of the invention the tension filament has a diameter larger than 0.050 inches. One embodiment of the invention has a tension filament with a diameter of 0.020 inches.

Figure 7:
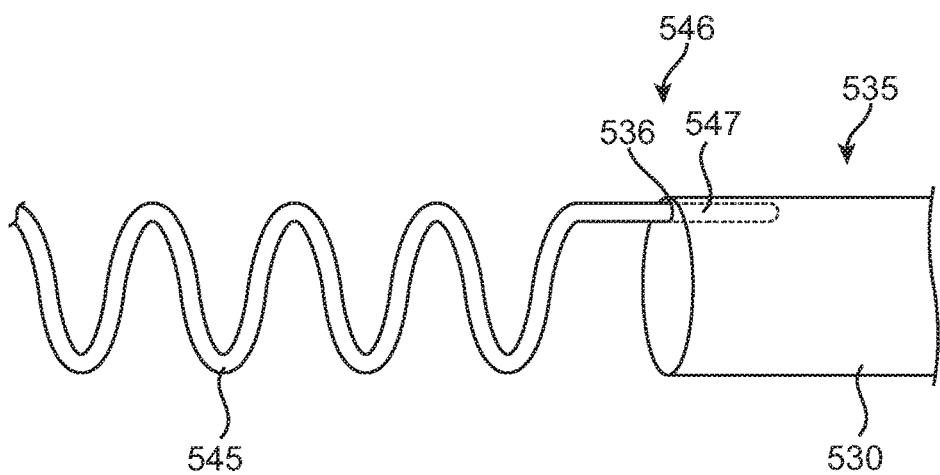
FIG. 7 illustrates the attachment of helical anchors to an helical anchor driver according to the current invention.

FIG. 7 illustrates another embodiment of a release mechanism according to the current invention. The helical anchor 545 has a proximal end 546 with a driver portion 547 that extends straight in a proximal direction from the helical anchor. The distal tip 535 of the driver has a hole 536 for placement of the driver portion of the helical anchor such that the helical anchor will fit snugly into the driver during implantation of the helical anchor. Once the helical anchor is implanted, the driver and delivery member are pulled away from the proximal end of the helical anchor and the straight driver portion of the proximal end is pulled from the hole in the distal tip of the driver. In some embodiments of the current invention, the length of the straight driver portion of the helical anchor can vary from 0.05 inches to 0.25 inches. Some embodiments of the current invention have helical anchors with straight driver portions that are longer than 0.25 inches, other embodiments of the current invention have helical anchors with straight driver portions that are shorter than 0.05 inches, and one embodiment of a helical anchor according to the current invention has a helical anchor with a straight driver portion of 0.10 inches.

In some embodiments of the current invention, the driver can be a hollow member having either a tension filament lumen or an anchor guide lumen communicating through its length. The helical anchor connections shown in FIG. 5 will work equally as well for tubular driver members as they will for non-tubular driver members.

Figure 8A:
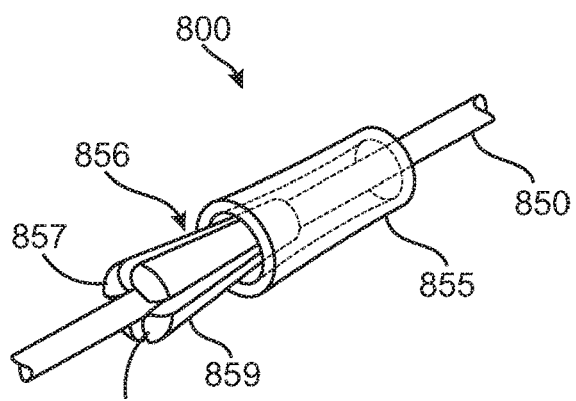
FIGS. 8A and 8B illustrate an embodiment of locking devices used for tensioning devices according to the current invention.
Figure 8B:
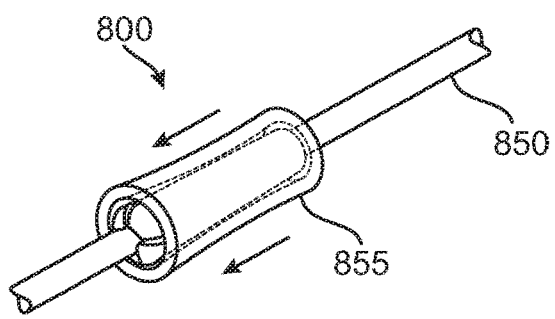

Referring now to FIGS. 8A and 8B, there can be seen a locking device 800 according to the current invention. Locking device 800 comprises a stop member 855 and a lock member 856. Stop member 855 has a size and shape that will prevent the stop member from entering the inner channel of a helical anchor. In some embodiments of the invention, the stop member 855 will be smaller than the outer diameter of a helical anchor but larger than the diameter of the inner channel. This will allow the stop member to be delivered through a delivery member or guide catheter.

Stop member 855 has at least one lumen communicating through the stop member. In the depicted embodiment, a lock member 856 has a lumen communicating through a proximal end there of such that the lock member can be placed on the filament 850 and slide along the length of the filament. The lock member 856 has a first end and a second end with a plurality of integral legs 857 that extend radially at an angle from the lock member. The legs of the lock member each have a slight lip 859 that will prevent the second end of the lock member from being completely inserted into the stop member.

The lock member is made from material having suitable flexibility to allow the legs to compress radially inward when the first end of the lock member is pushed or otherwise moved into the lumen of the stop member. The lumen of the stop member is sized such that when the lock member is inserted into the stop member, the legs of the lock member will be radially compressed against the tension filament. The legs of the lock member are sized and configured such that when the lock member is compressed inside the stop member, the tension filament is secured by the legs and the filament can not slide through the lock member.

FIG. 8B shows that as the lock member is pushed (in the direction of the arrows) along the tension filament 850, it is pushed into the stop member. Once the lock member has entered the stop member, it cannot move proximally along the tension filament in the direction of the arrows.

Once the anchors are planted in a valve annulus, a stop member and then a lock member are placed on each end of the tension filament. In one embodiment, the lock member is pushed into the stop member on one end of the filament outside of a patient's body and then the other end of the filament is pulled until the locking device is directly adjacent one of the helical anchors. A desired tension force is then applied to the tension filament. The force is maintained while the stop member and lock member on the other end of the tension filament are pushed along the filament such that the stop member makes contact with an implanted anchor and cannot move any further along the filament. The lock member is then pushed into the stop member to secure the tension filament such that the filament is under constant tension. The tension filament is then trimmed so that no unnecessary free ends of the filament extend beyond the locking devices.

Returning to FIG. 2, FIG. 2 shows a tensioning device of the current invention attached to a mitral valve annulus. Tension filament 250 is disposed in the inner channels of the helical anchors. In one embodiment, lock member 255A and 255B comprise a lock member such as lock device 800 illustrated in FIGS. 8A and 8B.

The tensioning device is delivered to a location adjacent the valve annulus using approaches described below. Once the delivery member is located at a position adjacent the valve annulus, the anchors are rotated into the valve annulus in the manner described above. Unless the procedure is being performed as an open heart procedure where the tension filament can be threaded through the anchors after implantation, the anchors must be implanted in the same order as the filament is routed through the anchors. Using the example of FIG. 2, the helical anchors can be implanted in alphabetical order 245A through 245E or they can be implanted in reverse alphabetical order. In one embodiment of the invention, the helical anchors are implanted so that the tension filament is threaded in to cross the valve from one valve leaflet to another valve leaflet in a zig-zag or generally "V" shaped pattern as illustrated in FIGS. 2 and 3, respectively. Once the anchors are implanted, the locking devices are attached to the filament as described above.

In at least one embodiment of the invention, a bead or similar device is attached to one end of the filament instead of a locking device such as locking device 800. The bead is then drawn tight against one of the anchors 245A or 245E, tension is applied and a locking device is placed against the other anchor of 2645A or 2645E as described above. The two sides of the annulus are then drawn closer together such that the shape of the annulus is changed and coaption of the valve leaflets is improved.

One exemplary method that can be used for accessing a patient's heart via minimally invasive surgical procedures to treat mitral regurgitation generally can start with intubating a patient with a double-lumen endobronchial tube that allows selective ventilation or deflation of the right and left lungs. The left lung is deflated, thereby helping to provide access to the surface of the heart. The patient is rotated approximately 30 degrees with the left side facing upwardly. The left arm is placed below and behind the patient so as not to interfere with tool manipulation during the procedure. While port positions depend to a large extent on heart size and position, in general a seventh and fifth space mid (to posterior) axillary port for tools and a third space anterior axillary port for the scope is preferable. A variety of endoscopes or thoracoscopes may be used including a 30-degree offset viewing scope or a straight ahead viewing scope. In general, short 10 to 12 mm ports are sufficient. Alternatively, a soft 20 mm port with an oval cross-section sometimes allows for two tools in the port without compromising patient morbidity.

In one embodiment of the present invention, passages are made through a patient's skin into the thoracic cavity. The passages may be formed by employing one-piece rods or trocars of prescribed diameters and lengths that are advanced through body tissue to form the passage, which are subsequently removed so that other instruments can be advanced through the passage. The passage may instead be formed by employing two-piece trocars that comprise a tubular outer sleeve, which is sometimes referred to as a port or cannula or as the tubular access sleeve itself, having a sleeve access lumen extending between lumen end openings at the sleeve proximal end and sleeve distal end. The two-piece trocar can further include an inner puncture core or rod that fits within the sleeve access lumen. The inner puncture rod typically has a tissue penetrating distal end that extends distally from the sleeve distal end when the inner puncture rod is fitted into the sleeve access lumen for use. The two-piece trocar can be assembled and advanced as a unit through body tissue, and then the inner puncture rod is removed, thereby leaving the tubular access sleeve in place to maintain a fixed diameter passage through the tissue for use by other instruments.

In one embodiment, a tubular access sleeve is placed through a passage that is made as described above in the chest wall of a patient. The selection of the exact location of the passage is dependent upon a patient's particular anatomy. A further conventional tubular access sleeve can be placed in a different passage that is also made in the chest wall of patient.

In accordance with one method used in the invention, the patient's left lung is deflated to allow unobstructed observation of the pericardium employing a thoracoscope or other imaging device that is inserted through a sleeve lumen of a tubular access sleeve. The thoracoscope or other imaging device may have its own light source for illuminating the surgical field.

A thoracoscope can then be inserted into the lumen of a tubular access sleeve to permit wide angle observation of the thoracic cavity by a surgeon directly through an eyepiece or indirectly through incorporation of a miniaturized image capture device (e.g., a digital camera) at the distal end of the thoracoscope or optically coupled to the eyepiece that is in turn coupled to an external video monitor. The thoracoscope may also incorporate a light source for illuminating the cavity with visible light so that the epicardial surface can be visualized. The thoracoscope may be used to directly visualize the thoracic cavity and obtain a left lateral view of the pericardial sac or pericardium over the heart.

The elongated access sleeve provides an access sleeve lumen, enabling introduction of the distal end of a pericardial access tool. The tubular access sleeve and the pericardial access tool are employed to create an incision in the pericardial sac so that the clinician can view and access the left free wall of the heart. After the clinician gains access to the heart, a continuous circular suture (commonly know and referred to herein as a purse string suture) is placed in the free wall of the left atrium at a location near the commisure of the mitral valve, and above the coronary sinus. The wall is then punctured inside the perimeter of the suture. The wall can be punctured using a puncture device, or the distal end of the delivery members described herein can be used to puncture the wall.

The distal end of a first delivery member can then be advanced through the elongated access sleeve, through the puncture formed through the myocardium, and placed against the mitral valve annulus. At least a fist anchor of a tensioning device for treating mitral regurgitation can then be implanted. Subsequent anchors can then be implanted using additional delivery devices or additional drivers in the same delivery device, tension is applied, and the device is secured, all as described above. The delivery member is then withdrawn and the purse string is tightened to close the puncture. The lung can then be inflated, the instruments withdrawn from the patient, and all openings closed. The procedure outside of the heart can be viewed through a scope as disclosed above, and the procedure inside the heart can be visualized and imaged using fluoroscopy, echocardiography, ultrasound, EM imaging, other suitable means of visualization/imaging, or combinations of the aforementioned visualization methods. Visualization techniques may also be used to map the heart prior to beginning the minimally invasive procedure. Mapping the heart provides details as to the size and shape of the valve annulus to be treated and the extent of deformation of the valve, itself.

Figure 9:
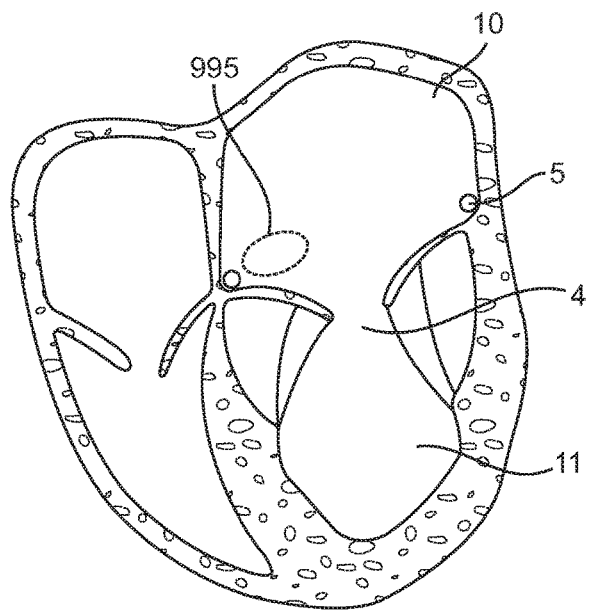
FIGS. 9 to 11 illustrate a minimally invasive surgical method for implanting tensioning devices to treat mitral regurgitation according to the current invention.
Figure 10:
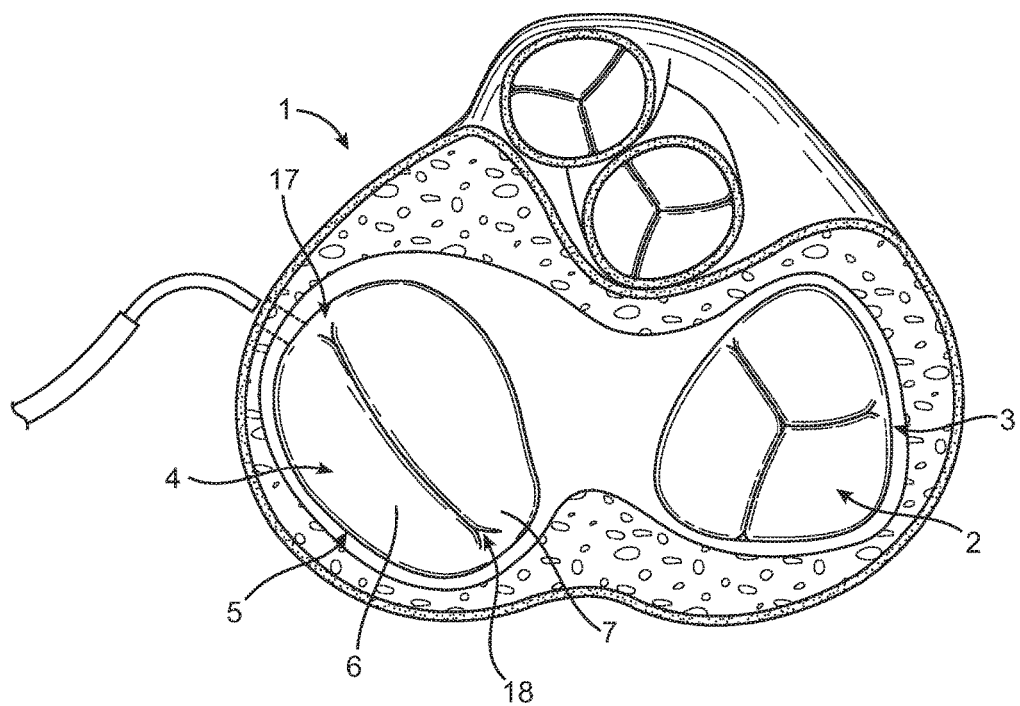
Figure 11:
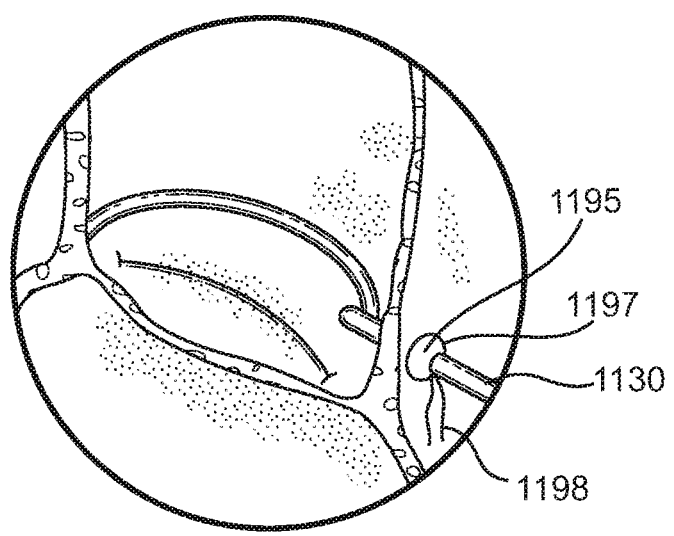

FIGS. 9, 10, and 11 illustrate an exemplary placement of delivery members of the current invention inside the heart using a minimally invasive surgical approach. FIGS. 9 and 10 are illustrations showing cross-sectional views of a heart 1 having tricuspid valve 2 and tricuspid valve annulus 3. Mitral valve 4 is adjacent mitral valve annulus 5. Mitral valve 4 is a bicuspid valve having anterior cusp 7 and posterior cusp 6. Anterior cusp 7 and posterior cusp 6 are often referred to, respectively, as the anterior and posterior leaflets. Also shown in the figure are the posterior commisure 17 and the anterior commisure 18. A purse string suture has been placed in the heart and the wall is punctured (as described above) at a location 995 in the atrium wall that is adjacent the posterior commisure 17 of the posterior and anterior cusp and above the coronary sinus. An elongated, generally tubular tensioning device delivery member can then be placed into the heart and positioned on the valve annulus for implantation of a tensioning device.

Referring particularly to FIG. 11, the location of the puncture site 1195 is visible inside of the purse string suture 1197 (the free ends 1198 of the which are visible in the figure), and a portion of a delivery member 1130 is illustrated for delivering a tensioning device to the posterior portion of a mitral valve annulus. A tensioning device, such as tensioning device 200 and 300, can them be placed in the valve annulus.

Figure 12:
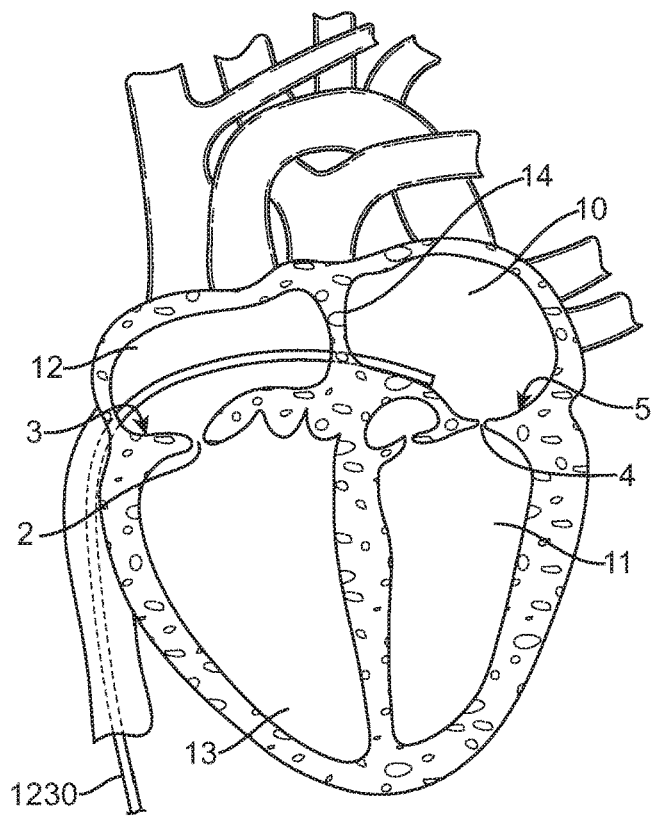
FIGS. 12 and 13 illustrate a catheter based method for implanting tensioning devices to treat mitral regurgitation according to the current invention.
Figure 13:
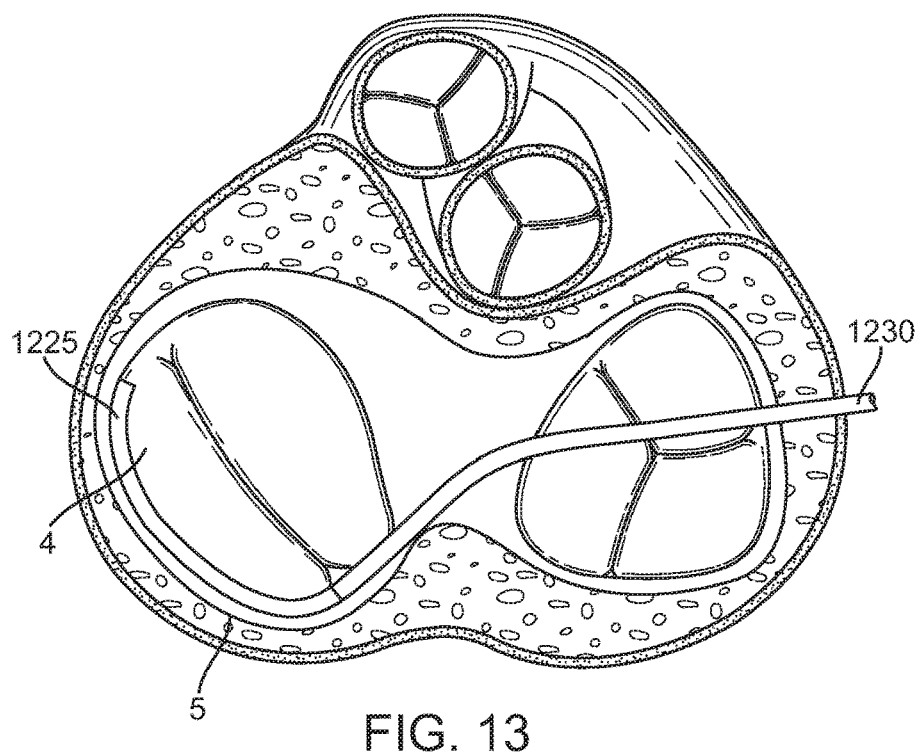

FIGS. 12 and 13 illustrate a catheter based approach for implanting a tensioning device. FIG. 12 is a longitudinal cross-sectional view of heart 1 having left atrium 10, left ventricle 11, right atrium 12, right ventricle 13, mitral valve 4, mitral valve annulus 5, tricuspid valve 2 and tricuspid valve annulus 3. An elongated delivery catheter 1230 having a tensioning device with helical anchors according to the current invention is shown with the distal end of the delivery catheter in the left atrium. When using a catheter based method for implanting a tensioning device, an elongate element (not shown), such as a guide catheter, having a lumen is first installed to provide a path for the tensioning device delivery catheter 1230 from the exterior of the patient to the left atrium. The tensioning device delivery catheter 1230 can then be advanced through the lumen so that the tensioning device can be implanted in a mitral valve annulus.

The device used for modifying the shape of the annulus is delivered using a catheter via the transeptal approach through the vena cava. The elongate element is inserted through the femoral vein into the common iliac vein, through the inferior vena cava into the right atrium 12. The transeptal wall 14 between the right atrium 12 and left atrium 10 is then punctured (preferably at the fossa ovalis) with a guide wire or other puncturing device. In one embodiment of the invention, a Brockenbrough® needle system as is currently known in the art can be used to puncture the septum.

Regardless of the method used to puncture the septum, the distal end of the catheter is advanced into the left atrium and the anchor guide 1225 is positioned adjacent the mitral valve annulus 5, as shown in FIG. 13. The tensioning device can then be advanced through the lumen of the elongate element to the mitral valve 4 for implantation into the mitral valve annulus 5. The anchor guide and helical anchor are advanced and rotated into the annulus.

Those skilled in the art will appreciate that alternative paths to gain access to the left atrium are available. For example, another possible path would be through the radial vein into the brachial vein, through the subclavian vein, through the superior vena cava into the right atrium, and then transeptally into the left atrium. Yet another possible path would be through the femoral artery into the aorta, through the aortic valve into the left ventricle, and then retrograde through the mitral valve into the left atrium.

Figure 14:
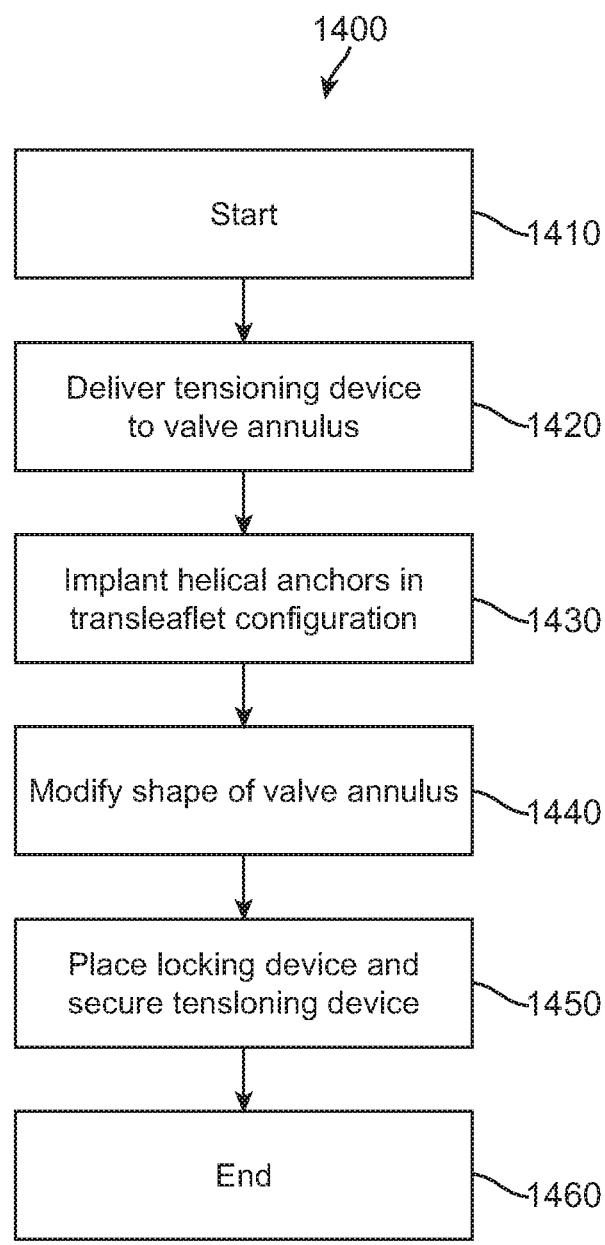
FIG. 14 is a flow chart showing one embodiment of a method for implanting a tensioning device according to the current invention.

FIG. 14 is a flowchart illustrating one embodiment of a method 1400 to modify the shape of valve annulus according to the current invention. Method 1400 begins at Block 1410. To practice the current invention, a clinician delivers a tensioning device to a location adjacent a valve annulus (Block 1420). The helical anchors are then implanted in a trans-leaflet configuration alternating from implanting an anchor on the anterior or posterior side of the annulus to an anchor on the opposite side of the annulus such that the elongated tension member crosses the mitral valve each time it is routed through a helical anchor subsequent to the previous helical anchor that the elongated tension member is routed through (Block 1430). The tension filament is then manipulated to apply a force to the implanted anchors and modify the shape of the valve annulus (Block 1440). Once a desire degree of modification has been achieved, a locking device is placed on the tension filament to secure the tensioning device (Block 1450). Method 1400 ends at Block 1460.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of treating mitral valve regurgitation, the method comprising:
    inserting a distal end of an elongated delivery catheter into a vessel;
    advancing the distal end through the vessel and into a left atrium;
    positioning the distal end adjacent a mitral valve annulus;
    sequentially deploying at least three anchors of a trans-leaflet tensioning device from the distal end to sequentially implant the at least three anchors into the annulus alternatingly on an anterior portion of the annulus and a posterior portion of the annulus;
    applying a tension force to a tension element of the tensioning device to alter the shape of the annulus to reduce regurgitation, wherein the tension element is coupled to the at least three anchors.

2. The method of claim 1, wherein the step of implanting the at least three anchors includes implanting at least one anterior anchor into the anterior portion of the annulus and implanting at least one posterior anchor into the posterior portion of the annulus such that at least a portion of the tension element comprises a trans-leaflet portion extending between the posterior and anterior anchors.

3. The method of claim 2, wherein tension on the tension element is exerted across the annulus by the trans-leaflet portion of the tension element to draw the posterior and anterior anchors closer together and thereby alter the shape of the annulus.

4. The method of claim 1, wherein the at least three anchors are helical.

5. The method of claim 4, wherein each helical anchor is implanted by rotating the respective helical anchor.

6. The method of treating mitral valve regurgitation according to claim 1,
wherein the step of inserting the distal end of the elongated delivery catheter into the vessel comprises inserting the distal end of the elongated delivery catheter into a radial vein, and
wherein the step of advancing the distal end through the vessel and into the left atrium comprises advancing the distal end through the radial vein, through a brachial vein, through a subclavian vein, through the superior vena cava, through a right atrium, through a septal wall puncture, and into the left atrium.

7. The method of claim 6, wherein the step of implanting the at least three anchors includes implanting at least one anterior anchor into the anterior portion of the annulus and implanting at least one posterior anchor into the posterior portion of the annulus such that at least a portion of the tension element comprises a trans-leaflet portion extending between the posterior anchor and the anterior anchor.

8. The method of claim 7, wherein tension on the tension element is exerted across the annulus by the trans-leaflet portion of the tension element to draw the posterior and anterior anchors closer together and thereby alter the shape of the annulus.

9. The method of claim 6, wherein the at least three anchors are helical.

10. The method of claim 9, wherein each helical anchor is implanted by rotating the respective helical anchor.

11. The method of treating mitral valve regurgitation according to claim 1,
wherein the step of inserting the distal end of the elongated delivery catheter into a vessel comprises inserting the distal end of the elongated delivery catheter into a femoral artery, and
wherein the step of advancing the distal end through the vessel and into the left atrium comprises advancing the distal end through a femoral artery, through an aorta, through an aortic valve, through a left ventricle, through the mitral valve, and into the left atrium.

12. The method of claim 11, wherein the step of implanting the at least three anchors includes implanting at least one anterior anchor into the anterior portion of the annulus and implanting at least one posterior anchor into the posterior portion of the annulus such that at least a portion of the tension element comprises a trans-leaflet portion extending between the posterior anchor and the anterior anchor.

13. The method of claim 12, wherein tension on the tension element is exerted across the annulus by the trans-leaflet portion of the tension element to draw the posterior and anterior anchors closer together and thereby alter the shape of the annulus.

14. The method of claim 11, wherein the at least three anchors are helical.

15. The method of claim 14, wherein each helical anchor is implanted by rotating the respective helical anchor.

16. The method of treating mitral valve regurgitation according to claim 1,
wherein the step of inserting the distal end of the elongated delivery catheter into the vessel comprises inserting the distal end of the elongated delivery catheter into a femoral vein, and
wherein the step of advancing the distal end through the vessel and into the left atrium comprises advancing the distal end through the femoral vein, through an iliac vein, through an inferior vena cava, through a right atrium, through a septal wall puncture, and into the left atrium.

* * * * *